United States Patent
Franques et al.

(10) Patent No.: US 8,632,187 B1
(45) Date of Patent: Jan. 21, 2014

(54) PROGRESSIVE MULTIFOCAL RIGID GAS PERMEABLE CONTACT LENS

(75) Inventors: Russell Franques, Sioux Falls, SD (US); Jeff J. Wittern, Sioux Falls, SD (US)

(73) Assignee: Dakota Sciences, Inc., Sioux Falls, SD (US)

( * ) Notice: Subject to any disclaimer, the term of this patent is extended or adjusted under 35 U.S.C. 154(b) by 701 days.

(21) Appl. No.: 12/762,347

(22) Filed: Apr. 18, 2010

Related U.S. Application Data (60) Provisional application No. 61/172,994, filed on Apr. 27, 2009, provisional application No. 61/173,579, filed on Apr. 28, 2009.

(51) Int. Cl.
*A61B 3/00* (2006.01)

(52) U.S. Cl.
USPC .......................................... 351/247; 351/246

(58) Field of Classification Search
USPC .......... 351/247, 200, 205, 206, 221, 222, 246
See application file for complete search history.

(56) References Cited

U.S. PATENT DOCUMENTS

| | | | |
|---|---|---|---|
| 2,164,801 A | 7/1939 | Dittmer |
| 2,641,161 A | 6/1953 | Silverstein |
| 3,195,145 A | 7/1965 | Tisher et al. |
| 2,618,200 A | 11/1965 | Clave et al. |
| 3,246,941 A | 4/1966 | Moss |
| 3,495,899 A | 2/1970 | Biri |
| 3,760,807 A | 9/1973 | Neefe |
| 4,194,815 A | 3/1980 | Trombley |
| 4,239,353 A | 12/1980 | Koller |
| 4,547,049 A | 10/1985 | Cotie et al. |
| 4,601,556 A | 7/1986 | Siviglia |
| 4,895,439 A | 1/1990 | Stoller |
| 4,952,045 A | 8/1990 | Stoyan |
| 4,997,268 A | 3/1991 | Dauvergne |
| 5,020,898 A | 6/1991 | Townsley |
| 5,085,013 A | 2/1992 | Ascosi et al. |
| 5,141,301 A | 8/1992 | Morstad |
| 5,191,365 A | 3/1993 | Stoyan |
| 5,349,395 A | 9/1994 | Stoyan |
| 5,788,957 A | 8/1998 | Harris |
| 5,929,968 A | 7/1999 | Cotie et al. |

(Continued)

FOREIGN PATENT DOCUMENTS

| | | |
|---|---|---|
| FR | 1299573 | 6/1962 |
| JP | 52-10742 | 1/1977 |
| JP | 52-77738 | 6/1977 |

OTHER PUBLICATIONS

The Contact Lens—Past, Present, and Future; Viscom Publications, Inc.; 1987 (20 pages).

(Continued)

*Primary Examiner* — Thomas K Pham
*Assistant Examiner* — Brandi Thomas
(74) *Attorney, Agent, or Firm* — Douglas W. Rudy (57) ABSTRACT

A contact lens is provided. It is a rigid gas permeable, corneal-scleral progressive, multifocal, vision lens that covers the cornea and a portion of the sclera of an eye. It is particularly beneficial for use on patients who have undergone refractive surgery and/or on patients experiencing presbyopia. The lens is designed to have dual touch contact with an eye. One contact point is the central portion of the cornea and the other contact point is a portion of the sclera.

7 Claims, 3 Drawing Sheets

(56) References Cited

U.S. PATENT DOCUMENTS

| | | | |
|---|---|---|---|
| 5,963,297 | A | 10/1999 | Reim |
| 6,543,897 | B1 | 4/2003 | Tung |
| 6,582,077 | B1 | 6/2003 | Tabb et al. |
| 2006/0152673 | A1* | 7/2006 | Cotie et al. ............... 351/160 H |
| 2009/0048670 | A1* | 2/2009 | Grierson et al. ............ 623/5.11 |

OTHER PUBLICATIONS

Dakota Sciences—Fitting Guide (2 pages).
Comparing RGP Multifocal Lens Designs—Contact Lens Spectrum, May 2002 (4pages).
AgingEye Times; 2003 (4 pages).
Bifocal and Multifocal Contact Lenses—Nancy Del Pizzo et al; AllAboutVision.com (4 pages).
Beyond the Limbus: Corneoscleral Lenses In Today's Contact Lens Practice—Dr. J. Jedlicka; Review of Cornea & Contact Lenses—Apr. 2008 (8 pages).
Gas Permeable (GP) Contact Lenses—Nancy Del Pizzo; AllAboutVision.com (3 pages).
Which Bifocal Design Is Right for You? www.contactlenses.org—(5 pages).
Proclear Multifocal Toric; www.coopervision.com 2009 (1 page).
Multifocal Contact Lenses—Liz DeFranco—www.allaboutvision.com (4 pages).
Bifocal and Multifocal Contact Lenses—Nancy Del Pizzo et al; AllAboutVision.com (4 pages) 2008.
Beyond the Limbus: Corneoscleral Lenses in Today's Contact Lens Practice—Dr. J. Jedlicka; Review of Cornea & Contact Lenses-Apr. 2008 (8 pages).
Multifocal Contact Lenses—Liz DeFranco—www.allaboutvision.com (4 pages) 2008.

\* cited by examiner

PROGRESSIVE MULTIFOCAL RIGID GAS PERMEABLE CONTACT LENS

CROSS REFERENCE TO RELATED APPLICATION

This application is claims the benefit of provisional Application 61/172,994, filed Apr. 27, 2009 and also to provisional Application 61/173,579, filed Apr. 28, 2009. Both applications are hereby incorporated by reference in their entireties.

BACKGROUND OF THE INVENTION

1. Field of the Invention

This invention is related to contact lenses and rigid gas permeable ("RGP") corneal-scleral contact lenses in particular. The lens set forth herein is a progressive vision lens designed to cover the cornea and a small portion of the sclera of the eye.

More particularly, the lens presented here allows for a near center aspheric addition to create a true progressive rigid gas permeable contact lens. The lens will correct for the lack of accommodation "presbyopia" in all eyes that are normal or unaltered and in eyes that have been altered by refractive surgery or any surgical procedure that modifies or changes the shape of the cornea such as transplants.

2. Description of the Art

The art in the contact lens field is replete with innovations in contact lens designs for both post refractive, bifocal and multifocal lenses. However, the application of a progressive multifocal corneal sclera lens that also allows a post refractive lens with the addition of a progressive multifocal in a corneal-scleral lens is unique. The aging population is growing worldwide. Today's refractive surgery patients in most cases had the procedure done to rid them of the need to wear spectacle lenses but as they age they develop presbyopia. This condition renders the eye with a decreasing amount of accommodation or the ability to transition from near to distance vision. The aging population is remaining active longer and requires a lens with continuous vision that can match their active lifestyle. The invention has been successfully used to provide corrections of a surgically altered cornea for myopia, hyperopia, and presbyopia. The lens, by its design, providing a progressive near center aspheric near addition with a diameter that covers both the cornea and a portion of the sclera, allows for a fit that corrects presbyopia in both normal and surgically altered corneas.

The lenses presented here work well in treating patients with visual deficiencies resulting from post refractive surgery errors and age related presbyopia in both normal and surgically altered eyes.

Furthermore, this invention relates to methods of the design and application of lenses and the means to obtain measurements from the eye by the use of pre-op and post-op keratometry readings, diagnostic lenses, topography readings and/or a combination of these.

Corneal contact lenses that are supported entirely on the cornea have problems that are solved through the use of a corneal-scleral lens as presented here. In a corneal lens all the functions of the lens take place on the cornea. This includes both near and distance vision, tear exchange curves for comfort, curves to center the lens and curves for edge contour. Each part of a corneal lens has a fitting duty and in some cases such as a translating or bifocal or multifocal. This presents a distinct problem such as vision and acuity loss during the transitional movement of the lens from the near and distance optical component of the lens. This results in a compromise to continuous vision correction. By placing a progressive multifocal segment in the center of the anterior surface of the lens the result is continuous vision throughout the transition from near to distance vision in a controlled rate. The larger diameter of the corneal-scleral lens, usually between 12.5 and 17.0 mm gives the lens its reliable centering. The larger diameter of the lens is also responsible for its high degree of comfort. This is possible as the edges of the lens are always under both the upper and lower eyelid minimizing the foreign body sensation as the eyelid performs its blinking function. It also increases comfort by distributing the weight and pressure of the lens over the cornea and a small portion of the sclera.

This application is related to rigid gas permeable contact lenses of the type set forth in U.S. Pat. No. 5,929,968 to Cotie and Hirshberg titled Scleral-Corneal Contact Lens which is incorporated by reference in its entirety herein. The lens set forth in U.S. Pat. No. 5,929,968 is a single vision lens for orthokeratology applications and is not a progressive multifocal rigid gas permeable lens.

In contact lenses there are designs to provide for bifocal vision. These designs include the most common type of bifocal contact, the translating bifocal. In this system eyelid contact with the lens will facilitate movement of the lens from a near object focus position to a distance power portion of the lens. In this example the near power is on the bottom of the lens. A system is used to keep the lens from rotating on the eye. When the patient looks downward to focus on a near object the lens translates up so the eye is looking through the near or add power at the bottom of the lens. When the person looks up and blinks the upper eyelid "catches" on the top portion of the lens forcing it downward allowing the patient to use the distance power portion of the lens. Because of the contact of the upper lid with the edge of the lens a comfort issue most often referred to as a foreign body sensation is caused. The use of the translating method also gives the unwanted lost of vision as the lens moves from distance to near during the blinking process.

In other methods of providing bifocal vision a mono vision situation is used to accomplish bifocal vision. This type of vision correction for presbyopes uses two single vision contact lenses one having the prescriptive power of the distance prescription in one eye and the other having the prescription for the near power in the other eye. The problem with this method is "simultaneous vision." This is were the eyes sees both near and distance at the same time. This method requires the patient to have an adaptation period were the brain is trained to see only the image that it requires and to ignore the other. This can in some patient cause a loss of depth perception. Some patients never fully adjust to this type of vision and the time of adaptation for those who can, varies from a short period of several days to a period of many days. Many patients simply discontinue the use of such contacts.

In this technique two single vision lens are used, one in each eye. One lens will have a prescriptive power of the distance prescription in one eye and the prescriptive power for the near power in the lens for the other eye. A refinement of this lens is to have one of the lenses being a bifocal lens however this has not proven to be a well accepted solution to the need for a bifocal contact lens.

Another method of vision correction in contact lens is the concentric bifocal that uses a system of corrective rings that alternate between near and far vision.

This method is also of the "simultaneous vision" mode where the brain is "seeing" both near and distance and the same time. This causes the patient to undergo the same type of adaptation problems as with monovision lens sets. The number of rings that are available to the eye is dependant upon pupil size, which will vary due to ambient lighting conditions. In most cases at least two rings are available.

With current small diameter rigid gas permeable lenses that float on the eye there is not enough stability for acceptable vision.

Each of these methods of providing bifocal vision have not been successfully and widely adopted as there are fit and comfort issues with each of these lens types. Only very motivated patients have been successful in continuing to wear theses types of lenses.

BRIEF SUMMARY OF THE INVENTION

The present invention provides, among other things, a rigid gas permeable lens that covers the cornea and a portion of the sclera of an eye. The lens is formed with a progressive vision prescription. This lens has a radial outer portion that generally conforms to the shape of the ocular surface in the scleral region. The posterior surface of the lens covering the corneal region of the eye is selectively spaced from, aligned with or in eyelid bearing pressure contact with the corneal region of the eye.

The effect of the stability of a lens using a larger diameter contact location is well known. The lens disclosed here uses the added stability inducing design of dual touch or dual contact. The inventors' lens has physical touch or contact on both the central portion of the cornea and a portion of the sclera. By affecting a touch pattern that comes in contact with two portions of the eye the lens of this design spreads the weight of the lens and the downward force of the eye lid onto two separate areas of the eye. This leads to a lens having increased comfort relative to other lenses on the market. Not only is comfort increased but this lens design also adds greatly to the stability of the lens afforded by this design. Because of the high Dk (oxygen transmitting or permeability) materials used in the production of the lens disclosed herein movement can be restricted and still maintain healthy corneas. This allows the vision correcting and fitting curves to maintain the positions that they were designed to be in. This increases visual acuity, and the total eye health as it pertains to the wearing of contact lenses.

The invention is directed to solving the problems of both the person that has had refractive surgery or non-altered corneas and those that are now experiencing the effects of presbyopia. Either problem can be addressed by the use of the lenses disclosed herein. Presbyopic eyes need more oxygen, have less corneal sensitivity, increased positive spherical aberrations and may see poorly in low light. A presbyopic eye also experiences increased light scatter resulting in glare, and may have a smaller pupil size. Also the post refractive surgery eye will generally have a flatter optical zone with more normal peripheral area and can experience increased glare especially at night. Another problem post refractive surgery is the possibility of developing a condition known as ectasia. The lenses provided by this invention recognize these post refractive surgery possibilities and provide a cornea-scleral lens that improves the vision of the person with some of these maladies. All of the above conditions respond favorably to the use of a corneal-scleral progressive multifocal lens including but not limited to patients with post refractive surgical problems.

The lenses of this invention can be manufactured from a variety of materials including soft and GP and PMMA materials. GP materials of high DK values are the preferred medium because of the better visual acuity that is obtained by using a material that is more stable and has little to no flexure and because of its high oxygen transmission that provides excellent eye health.

This type of contact lens have not been doable until now because of the lack of a large diameter lens that provided a solid workable platform to place the aspheric add zone on the convex side of the lens. With a scleral corneal lens the lens is well stabilized on the eye allowing for a true progressive multi-focal RGP contact lens.

One object of the lens is to provide a progressive multifocal lens that can be worn by patients with emerging presbyopia and patients with more advanced presbyopia with or without surgical alteration to the cornea.

One object of the invention is to provide a post refractive lens with the addition of a progressive multifocal in a cornea-scleral lens.

Another object of the invention is to provide a lens that provides corrections of a surgically altered cornea for myopia, hyperopia, and presbyopia.

Also an advantage of the lens presented here is the feature of the lens limiting, because of its larger diameter of the lens, the exposure of the wearer's eye to the harmful effects of ultraviolet radiation on a larger portion on the eye and it structures.

Another advantage is that true progressive multi-focal prescriptions are can be translated into soft lenses.

Another advantage of this lens is that there is near "instant vision" when changing focus from a near object to an intermediate or far object, and vice-versa.

Another advantage of the invention is that it allows for a near aspheric center addition in an RGP corneal-scleral contact lens.

A further advantage of the lens presented here is that the lens helps to protect the sensitive T cell regeneration area of the eye by aligning with or vaulting the limbus.

Another advantage of this lens is that it is comfortable to wear since the lens fits under both the upper and lower eye lid eliminating the foreign body sensation during the blinking process.

Also an advantage to this lens is that it is not prone to unintended dislodgement during periods of physical activity making it useful for patients involved in sports.

Another advantage over soft lenses is the loss of visual acuity during the blinking process with can cause a soft lens to "fold" or distort causing a loss of clear vision during periods of physical activity. This making it desirable for many sports activities that can be enhanced by vision that is not compromised by loss of continues vision.

Another advantage of the lens is that it offers a unique combination of visual and comfort benefits not available in contact lenses to date.

One object of the invention is to provide a lens that can be worn after surgical treatment of the cornea such as post refractive surgery or corneal transplants surgery.

Another object of the invention is to provide a lens with progressive multi-focal capability to address presbyopia.

Both of the above objects can be used separately or combined together.

Another object of the invention is to provide a lens with progressive multi-focal capability to address the effects of presbyopia that may set in after refractive surgery.

Another object of the invention is to provide a lens giving a wearer continuous vision that can match the active lifestyle of aging wearers.

Another object is to provide a contact lens that is comfortable to wear and easy to insert and remove.

A further advantage of this lens is that it is thinner and much smaller than previous scleral contact lenses. This lens conforms to the cornea and a small portion of the sclera to provide a distributed bearing area for the lens.

It is an object of the invention to provide a lens that is not easily dislodged.

Also an advantage is that visual performance is consistent with rigid designs.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. §112, ¶ 6. Thus, the use of the words "function," "means" or "step" in the Detailed Description or Description of the Drawings or claims is not intended to somehow indicate a desire to invoke the special provisions of 35 U.S.C. §112, ¶ 6, to define the invention. To the contrary, if the provisions of 35 U.S.C. §112, ¶ 6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶ 6. Moreover, even if the provisions of 35 U.S.C. §112, ¶ 6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE DRAWINGS

Referring to the detailed description when considered in connection with the following illustrative figures may derive a more complete understanding of the present invention. In the figures, like reference numbers refer to like elements or acts throughout the figures.

FIG. 5 is a process flow chart showing the normal fitting and manufacturing of the lens of the invention.

Elements and acts depicted in the figures are illustrated for simplicity. They are presented to illustrate the invention to assist in an understanding thereof. The figures have not necessarily been rendered according to any particular sequence, size, scale or embodiment.

DETAILED DESCRIPTION OF THE INVENTION

In the following description, and for the purposes of explanation, specific details are set forth in order to provide an understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the invention is not limited to the examples that are described below.

This invention incorporates a design that will provide optical correction for an eye that has developed presbyopia and also for an eye subsequent to surgical treatment of a defined portion of the cornea and the onset of presbyopia. The contact lens presented here has a central area that is adapted to be optically aligned with the lens of the eye and provides optical correction to light passing through the eye lens. The lens has a posterior surface in substantial abutment with a corresponding predefined surface of the cornea. In the post refractive surgical design the lens has an intermediate portion surrounding the central portion that has a posterior surface that is spaced from the surface of the surgically treated portion of the cornea, and a peripheral portion that has a posterior surface in substantial abutment with a predetermined surface area of the sclera of the eye. The central and peripheral portions of the posterior surface of the lens cooperate to control and distribute the bearing pressure imposed on the lens by an eyelid when the eyelid is moved over the anterior surface of the lens.

In the design to fit non-surgically altered corneas the above design is the same only it is fit over the center of a non-altered cornea. This design is for normal eyes that have an un-altered cornea.

The anterior surface of the lens is fitted with an aspherically designed segment centrally located at a pre-defined diameter that provides correction for an eye that is experiencing presbyopia. This aspherically designed segment is located in a predefined central area that is adapted to be optically aligned with the lens of the eye and provide optical correction to light passing through the eye lens for near vision correction.

In the design of this lens there is a range of parameters that are used in the final embodiment of the lens. It has been found that a standard curve ranges of the fitting set can range from 7.34 mm to 8.33 mm for the progressive multifocal set.

It is also known by the inventors that the range of the lenses that can be produced is limited only by the combination of the prescriptive power, diameter, and lathe or other processing equipment range. Extremely flat and high curves are possible because of the fitting diameters that place the lens touch on both the cornea and the sclera.

Sagittal depth for this lens is dependent upon the peripheral curve that is chosen during the lens fitting of a particular patient. This is important because after fitting the peripheral curve/sclera portion of the lens a base curve is chosen that will fit the central portion of the cornea without altering the sagittal height of the lens. This allows the practitioner to know how the lens will ultimately fit when both the peripheral curve portion and the base curve portion are married together to form the final lens.

Zone sizes for each lens is dependent upon the prescription and the peripheral and base curves that will be married together. The adjustment of each curve places the correct curve in the correct areas of the cornea and sclera so to best fit these areas and allow the lens to contour to the total geometry of the eye and achieve high stability. The zone sizes in the optical center are dependent upon the choice of the fitting set lens that was chosen for the peripheral curve. Adjustment of the curve zone size allows the lens to maintain the same sagittal height when adding steeper or flatter base curves.

In this lens development add zones and powers are determined by the prescription that was produced by the practitioner during the refraction process of the eye exam. A determination is made as to which eye is the dominant eye. Next a determination of the initial add zone size, by using the diameter of the pupil of the eye in normal room illumination, will be made. This dilating of the pupil is the process that allows the eye to transition from near to distance vision. The non-dominant eye will have a larger initial add zone size by 0.50 mm.

The add power is determined by the spectacle add power determined during the eye exam. In the dominant eye we will use an add power that is 0.50 D less than the spectacle add. In the non-dominant eye we will use the full spectacle add power.

The lens of this invention can be made in the diameter range of from about 13.0 mm to about 16.0 mm. This range will cover the range from a micro cornea to an extra large cornea. This gives the lens an optimal range that will allow the prescriptive and landing curves to be placed in the area that will provide the best vision, eye health, and comfort.

Because of the aspheric design of the center addition power the disclosed lens provides the patient continuous vision from distance to near. Such continuous vision cannot be accomplished with other types of multifocal contact lenses, such as, but not limited to, the translating lens in which the lens must move from its distance component to the near vision component causing the loss of clear vision during the translation from distant to near vision. The design of the aspheric center addition gives the patient clear, accurate vision throughout the range from near to distance when fit correctly.

The lens of this invention also allows a patient that has had refractive surgery for health or cosmetic reason to continue to wear contact lenses. This has the potential to include a large portion of the population that has had refractive surgery the opportunity to remain in contact lenses for both health and cosmetic reasons. The geometry of the eye after surgery has been altered in a treatment zone in the center of the cornea. Because this lens is a larger diameter it provides great fitting flexibility for patients with surgically altered eyes. The standard smaller corneal lenses that sets only on the cornea has a much harder time adapting to the large changes in geometry between the treatment area and the non surgically altered portion of the eye.

The corneal-scleral progressive multifocal post refractive surgical lens is formed from a high Dk rigid gas permeable material and has a flat central posterior surface (base curve). This flat area, also known as a reverse curve, is flatter than the remaining three curves, namely the secondary curve, the intermediate curve, and the peripheral curve. These last three curves are steeper than the base curve. This design allows the fitting of the portion, the treatment area, of the cornea that has been ablated during refractive surgery.

This lens has been found to be more comfortable to wear than a conventional contact lens for both patients with normal refractive errors and those who have had refractive surgeries. The lens presented here is designed to rest on the eye under both the upper and lower eyelid. Because the lens is already under both lids the feeling of a foreign body being in the eye is greatly reduced. This causes the lens to be extremely comfortable. In older designs that were smaller and rested entirely on the cornea, the upper and lower eyelids made contact or bumped into the edge of the lens each time the eye blinked. This blink contact with the edge of a lens causes an uncomfortable sensation that led many patients to discontinue use of conventional contact lenses.

Three methods of fitting the posterior surface of the lens to the eye are available.

A first fitting procedure when fitting the post refractive design involves using the pre-surgical keratometer reading of the eye before the surgical procedure was preformed for the secondary, intermediate, and peripheral curves. Then assessing the keratometer readings of the treatment zone of the post surgical cornea to be used for the base curve.

The second method which is the preferred method for both standard and post refractive corneas is to use a fitting set or a set of diagnostic lenses to determine the best fit of the secondary, intermediate, and peripheral curves. For the standard refractive error cornea fitting the central cornea or base curve with another or the same lens from the fitting set to yield a correct fit. For the post refractive surgery patient the practitioner will then use the keratometer readings of the post surgically altered treatment area to adapt the base curve to fit.

The third method is to use a specifically designed diagnostic lens set to fit both the surgically altered treatment area and the secondary, intermediate, and peripheral curves.

The anterior surface of the lens contains the addition or segment that provides for the correction for the near and intermediate reading distances. This is fit by determining the base refraction for distance vision and addition power for the anterior aspheric segment for near vision. Then measuring the pupils of both eyes in normal room illumination to determine the size of the add zone. The dominant eye must also be ascertained. Using the above information the bifocal can then be determined.

When an object is held at a distance the pupil dilates to a larger diameter effectively utilizing the distance portion of the lens. An object held closer to the eye will dilate the pupil to a smaller diameter effectively utilizing the near portion of the lens.

The post refractive design of this invention will provide optical or visual correction for the lens of the eye after surgical treatment, such as a radial keratotomy, Lasik (laser in situ keratomileusis), or any other surgical treatment of the eye that changes the shape of the cornea. For example, when used after failed corneal surgery, or as an adjunct to partially successful surgery, the intermediate portion of the lens is desirably spaced from the surgically treated corneal surface. The eyelid bearing pressure is controllably distributed over the scleral and central corneal surfaces. If it is desired to flatten the central corneal region, the corresponding area of the posterior surface of the lens is desirably flattened, that is has a larger radius or curvature than the ocular surface of the central cornea.

For those eyes that have been modified by surgical treatment to the cornea to correct vision and are now suffering from presbyopia, the addition of an aspherical surface of predetermined diameter and curvature is added to the anterior surface of the lens to correct for deficiencies' in near vision.

Figure 1:
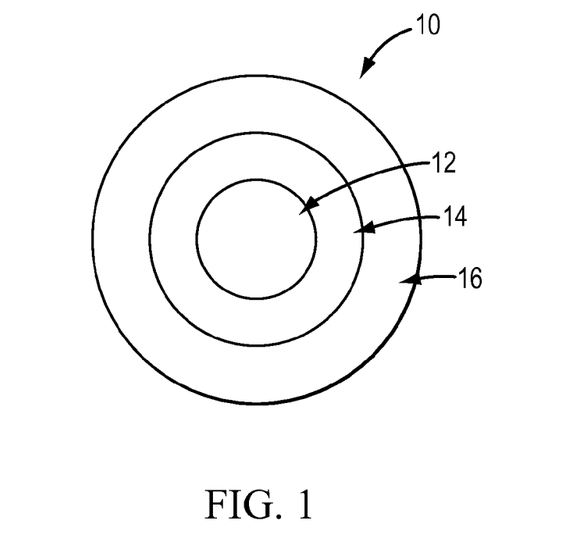
FIG. 1 is a lens showing the sections of the lens directed to near, intermediate and distance prescription corrections.
Figure 2:
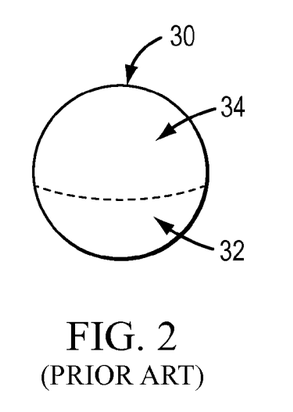
FIG. 2 is a presentation of a known style of translating lens.
Figure 3:
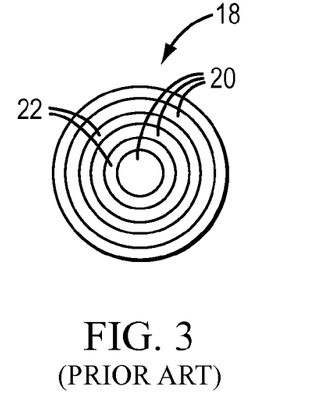
FIG. 3 is a presentation of a known style of concentric lens.
Figure 4:
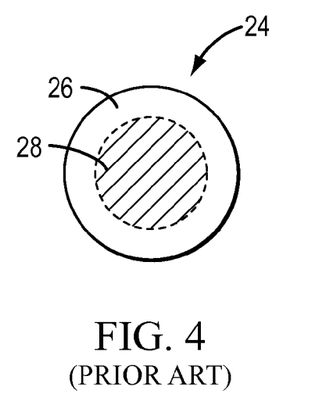
FIG. 4 is an illustration of an aspheric lens.

Turning to FIG. 1. This is the lens of the invention shown generally as 10. FIGS. 2-4 are lenses known in the art and are discussed below.

The lens of this invention is a rigid gas permeable lens ("RGP" lens). FIG. 1 is a representation of an aspheric multifocal contact lens where both distance and near prescriptions are placed in the central visual area, on or close to the pupil. The lens 10 will cover the cornea and a portion of the sclera while bridging the limbus. This lens is designed to vault or align with the limbus. The design helps to protect the sensitive T cell regeneration area of the eye. By aligning with or vaulting the limbus pressure on this area is eliminated. Having the periphery of this lens touch the sclera of the wearer's eye makes this lens different from the lenses currently being made. None of the lenses known to the inventors are aspheric multifocal lenses that cover the cornea and at least a portion of the sclera. The front surface, by the addition of a multifocal structure, is designed to provide continuous vision, that is, constant progressive vision, in the near, intermediate, generally 14, and distance, generally 16 fields of view. The front surface of the lens has an adjustable aspherical central zone that is calculated by measuring the wearer's pupil diameter in normal room illumination, which is than designed to provide near vision, generally 12. The front surface also incorporates an adjacent adjustable spherical portion that is designed to provide distance vision, generally 16. Because of the unique nature of the concave side of the lens and large diameter (13.3 mm to 16.0 mm) which by design minimizes movement has allowed the use of the near center add to be very effective. The movement of the patient's gaze is the control mechanism in moving from distance to near vision. When the wearer views and object at a close distance the pupil dilates down to a small aperture allowing the wearer to see through the central portion 12 of the lens which is the addition ("add") area used for reading or close work. When the wearer views an object in the distance the pupil dilates to include the distance portion of the lens 16 and give excellent distance vision. As the wearer's gaze moves through the intermediate distance range the aspheric portion of the lens, generally 14, also provides vision in the zones that would include tasks, such as, for example, but not limited to, computer use. Other attempts using a near center add have not been successful because of movement of the lens in general and folding of the lens (in the case of soft contact lenses). This misalignment has limited the wearer's ability to use the near and distance zones effectively causing blurred vision. The aspherical near and the spherical distance portions on the convex surface of the lens merge in a progressive design to avoid a stark juncture and provide continuous vision between distance intermediate and near objects.

This lens design allows diopter additions on the front surface of the lens.

This rigid gas permeable multifocal design is placed on the convex portion of the lens and is designed to work more like a progressive eyeglass lens where the different prescriptive powers are lathed in an aspherical and spherical design to provide continuous vision throughout the movement of the wearer's gaze from distance to near vision. This technique more closely emulates the eye before the onset of presbyopia.

Spherical center add uses a method in which a near power of varying size is lathed in the center of the contact lens. The rest of the optical portion of the lens in lathed to provide distance vision. This design works better than the others detailed below in the discussion of FIGS. 2-4 but because of the spherical nature of the lens it can only provide distance and near vision. The distance and near only design leaves out the important intermediate vision area that persons having presbyopia require in order to allowing them the use computers and other devices that require intermediate vision.

FIG. 2 is a depiction of a known translating lens, generally 30. In this lens the near 32, and far 34, prescription zones are distinct. The wearer's pupil moves from one zone to another depending on the wearer's visual need at the moment. In this translating lens the near prescription 32 is usually placed at the bottom of the lens. The distance prescription 34 is placed at the top of the lens. This is similar to bifocal eyeglasses. In some situations this is reversed and the near prescription is place at the top. This may be beneficial depending on the needs of a wearer's work or hobby.

Translating lenses, such as shown in FIG. 2, may rotate when the wearer blinks. Thus some translating lenses are weighted or ballasted, at the bottom to keep the lens properly positioned on the wearer's eye. Another way of controlling a translating lens is to have it flattened or truncated at the bottom. In this embodiment the lower eyelid will support and shift the lens upward when the wearer needs access to the near vision zone.

Translating lenses are more adaptable to small pupils although they can accommodate large pupils, but not as effectively. Translating lenses also have other problems not inherent in the instant invention. These include the need for a translating lens to move freely on the eye in order to re-center. Wearers with habitual dry eyes are not good candidates for translating lenses. Another problem with translating lenses is that weakened muscle capability in upper eyelids may allow the eyelid to interact with the lens too much. This may be problematic in older wearers.

FIG. 3 is a representation of a concentric or annular lens, generally 18. In this style of lens the near and distant prescriptions are formed on the lens in a bull's-eye pattern of concentric rings. The near correction, such as center and rigs 20, may be in the middle of the lens with the distance prescription in the other rings such as 22. Alternatively these locations can be reversed. Placement is dependent on the lifestyle of the wearer or, in some situations, the pupil size of the subject. Large pupils will have the near prescription in the center. For intermediate vision a third zone or ring will be formed between the center section and the outer ring. This extra ring will create a multifocal contact lens. A blending of the edges of the zones is possible.

FIG. 4 is a bifocal contact lens called an aspheric multifocal contact lens, generally 24. In this lens, known in the prior art, both distance and near 28 prescriptions are placed in the central visual area, on or close to the pupil. When the aspheric multifocal contact lens wearer gazes at an object in the distance the wearer learns to ignore near objects. When the wearer focuses on a near object the wearer will learn to ignore far away objects.

The progressive multifocal lens of this invention is preferably manufactured from a material that contains an ultraviolet absorption component. Because of the large diameter of the lens this ultraviolet absorption component adds greater protection to the eye by the fact that the lens covers the cornea and part of the sclera. This feature aids in limiting the exposure of the eye to the harmful effects of ultraviolet radiation.

FIG. 5 is a process flow chart that shows the progression of a lens selection and manufacturing process used in the production of a lens for a particular patient. This chart starts a to point where a patient walks into a doctor's office with the intent of getting fitted for contact lenses that will accommodate patients that have unusual needs relating to fitting contacts. For instance, this lens is helpful in fitting postoperative eye surgeries, for example. The various acts in the process of providing a lens to a patient begins with determining if the subject or patient has undergone refractive surgery. If the answer to this question is "yes" that patient would be a good candidate for the fitting of the lenses disclosed herein. If the answer is "no" than the next question would be whether or not the patient is presbyopic. If the answer to that question is "yes" than the lens is a good option. If the answer is "no" the patent may still want or have a need for this lens however other lens options are also available. It should be noted that these two decisions can be independent or combined. That is a patient can be fitted with either or both progressive or PRS lenses.

If the answer to either of the above questions is 'Yes" than the doctor or technician should proceed with fitting of PRS progressive lenses.

The next act is to fit the patient with the standard set of fitting lenses. These lenses will have a range of diameter of approximately 7.34 to approximately 8.33 mm in diameter. The doctor will select the lens that fit best at the periphery.

In the next act the doctor will determine a base curve in relation to current K readings of the treatment area followed by determining the spectacle add and add zone size based on patient's pupil size which can range from small at 1.5 mm, to medium at 2.0 mm and to large at 2.5 mm.

After the fitting is accomplished by the doctor or technician the appropriate lens is ordered from a manufacturing laboratory with the selected PC, base curve, power add, zone size and material. The laboratory will insert these parameters in the focal points. With these specifications fixed the laboratory can proceed with manufacturing a lens.

The laboratory will select a lens button; buttons of the type used in these lenses are available from Bausch and Lomb Company, and load the lens button in the lens processing equipment such as a lathe. A job ticket with the desired data for the lens is scanned or read by the lens processing equipment and the equipment is ready to form the lens. A backside or concave side of the lens is formed first. The button is attached to an arbor with the backside of the lens attached to the arbor by "blocking" using a water soluble wax compound as a the agent for affixing the button to the arbor. In this act the lens is centered by the blocking procedure for processing the front side of the lens.

The arbor is placed in the processing equipment, again this can be a lathe in one embodiment, the work ticket is scanned for processing data and the equipment will process the front side of the lens. On completion of the manufacturing process the arbor and lens are removed from processing and placed in an ultrasonic bath to deblock the completed lens from the arbor. After this process is complete the lens will be checked for correct power, thickness, and diameter and if it is satisfactory the lens will be shipped to the account that ordered the lens.

The acts above are the usual acts performed in selecting and processing a lens from start to finish however there may be nuances of process flow that are slightly different from the above depending on unusual factors related to the processing of a lens. The above is not intended to be a limitation on the possible process flow but is intended to show one way that the process can be performed.

In summary the invention herein is directed to a rigid gas permeable progressive corneal-scleral contact lens comprising a lens having sufficient diameter to cover the cornea and a portion of the sclera of an eye. This lens has an anterior surface with a multifocal segment including an aspheric central zone designed to provide near vision. It also includes a spherical portion to provide distance vision adjacent the aspherical central zone. This allows the lens to provide near center aspheric addition on a true progressive rigid gas permeable contact lens. Continuous vision results throughout the transition from near to distance vision in a controlled rate as the multifocal segment in the center of the anterior surface of the lens is a progressive multifocal segment.

The large diameter of the corneal-scleral, on the order of approximately 12.5 mm to approximately 17.0 mm, facilitates the edges of the lens always being under the upper and the lower eyelids of the wearer's eye.

The large diameter of the lens, when the lens is provided with an ultraviolet absorption component also provides the benefit of adding protection from ultraviolet light to the eye as the lens covers the cornea and part of the sclera.

While the invention is described herein in terms of preferred embodiments and generally associated methods, the inventor contemplates that alterations and permutations of the preferred embodiments and methods will become apparent to those skilled in the art upon a reading of the specification and a study of the drawings.

Another way of summarizing the invention is to say that the invention is a rigid gas permeable progressive corneal-scleral contact lens, having an anterior surface and a posterior surface, for fitting to an eye. This special lens is a rigid gas permeable lens of sufficient diameter to cover the cornea and a portion of the sclera of the eye with the radial outer portion of the lens conforming generally to the shape of the ocular surface of the eye in the scleral region of the eye. The posterior surface of the lens covers the corneal region of the eye is selectively spaced from, aligned with, or in eyelid bearing pressure contact with the corneal region of the eye. In essence this provides a dual contact lens that contacts the central portion of the cornea and simultaneously contacting the sclera. This lens conforms to the cornea and a small portion of the sclera to provide a distributed bearing area for the lens. The large diameter of the lens provides a solid workable platform for an aspheric add zone on the convex side of the lens resulting in a true progressive multi-focal rigid gas permeable lens. The anterior surface of the lens has an aspherical segment centrally located at a pre-defined diameter that provides correction for an eye that is experiencing presbyopia, the lens adapted to be optically aligned with the lens of the eye and provide optical correction to light passing through the eye lens for near vision correction.

The inventors have described the invention above. However, neither the above description of preferred exemplary embodiments nor the abstract defines or constrains the invention. Rather, the issued claims variously define the invention. Each variation of the invention is limited only by the recited limitations of its respective claim, and equivalents thereof, without limitation by other terms not present in the claim.

What is claimed is:

1. A method of fitting the posterior surface of a corneal-sclera progressive multifocal rigid gas permeable lens to a post refractive surgery eye, the corneal-sclera progressive multifocal rigid gas permeable lens having sufficient diameter to cover the cornea and a portion of the sclera of an eye, the method comprising the acts of:

performing and recording a pre-surgery keratometer reading of the eye;

using the pre-surgical keratometer reading of the eye for determining secondary, intermediate, and peripheral curves;

assessing the keratometer readings of the treatment zone of the post refractive surgical cornea to be used for the base curve;

using fitting set lenses to determine the fit of the anterior surface of the lens having a multifocal segment that is an aspheric central zone to provide near and intermediate vision and a spherical portion to provide distance vision adjacent the aspheric central zone using a center aspheric addition resulting in a lens that gives true continuous vision through near, intermediate, and distance vision zones.

2. A method of fitting the posterior surface of a corneal-scleral progressive multifocal rigid gas permeable lens of sufficient diameter to cover the cornea and a portion of the sclera to an eye wherein a keratometer reading of the eye was performed as part of an initial eye exam comprising the acts of:

using the keratometer readings to adapt the base curve to fit;

acquiring a fitting set of lenses to determine the best fit of the secondary, intermediate, and peripheral curves, the fitting set lenses for determining the fit of the anterior surface of the lens, the lens having a multifocal segment that is an aspheric central zone to provide near and intermediate vision and a spherical portion to provide distance vision adjacent the aspheric central zone using a center aspheric addition resulting in a lens that gives true continuous vision through near, intermediate, and distance vision zones;

fitting lenses from the fitting set to the eye to determine the best fit of the secondary, intermediate, and peripheral curves;

fitting the central cornea or base curve with another or the same lens from the fitting set to yield a correct fit.

3. The method of claim 2 wherein the method is for fitting the posterior surface of a multifocal lens to a post refractive surgery eye, further comprising the acts of:

acquiring keratometer readings of the post surgically altered treatment area of the post refractive surgery eye;

using the keratometer readings of the post surgically altered treatment area to adapt the base curve to fit the post refractive surgery eye.

4. The method of claim 1 wherein the diameter of the corneal-sclera progressive multifocal rigid gas permeable lens has a diameter of approximately 12.5 mm to approximately 17.0 mm to simultaneously contact the central portion of the cornea and the sclera to provide a distributed bearing area for the lens and further providing a workable platform for an aspheric add zone on a convex side of the lens.

5. The method of claim 1 wherein the corneal-sclera progressive multifocal rigid gas permeable lens comprises an ultraviolet absorption component whereby due to the large diameter of the lens the ultraviolet absorption component adds protection from ultraviolet light to the eye as the lens covers the cornea and part of the sclera.

6. The method of claim 2 wherein the diameter of the corneal-sclera progressive multifocal rigid gas permeable lens has a diameter of approximately 12.5 mm to approximately 17.0 mm to simultaneously contact the central portion of the cornea and the sclera to provide a distributed bearing area for the lens and further providing a workable platform for an aspheric add zone on a convex side of the lens.

7. The method of claim 2 wherein the corneal-sclera progressive multifocal rigid gas permeable lens comprises an ultraviolet absorption component whereby due to the large diameter of the lens the ultraviolet absorption component adds protection from ultraviolet light to the eye as the lens covers the cornea and part of the sclera.

* * * * *